United States Patent [19]

Fisher

[11] 4,093,629

[45] June 6, 1978

[54] DERIVATIVES OF ANTIBIOTIC SUBSTANCE MILBEMYCIN AND PROCESSES THEREFOR

[75] Inventor: Michael H. Fisher, Bridgewater, N.J.

[73] Assignee: Merck & Co., Inc., Rahway, N.J.

[21] Appl. No.: 786,172

[22] Filed: Apr. 11, 1977

[51] Int. Cl.$^2$ .......................................... C07D 493/22
[52] U.S. Cl. ........................ 260/326.34; 260/343.41; 424/279; 424/274
[58] Field of Search ....................... 260/343.41, 326.34

[56] References Cited

U.S. PATENT DOCUMENTS

| | | | |
|---|---|---|---|
| 3,950,360 | 4/1976 | Aoki et al. | 260/343.41 |
| 3,984,564 | 10/1976 | Aoki et al. | 260/326.34 |

OTHER PUBLICATIONS

Wagner & Zook, Synthetic Organic Chemistry, John Wiley & Sons, Inc., New York 1953, pp. 484, 169.
House, Modern Synthetic Reactions, W. A. Benjamin, Inc., Menlo Park, Calif., 1972, p. 481.
Mishima et al., Tetrahedron Letters, pp. 711–714, 1975.
Derwent Abstracts, 76268w/46, to Sankyo Co., Ltd., Abstract Japanese Patent Application 29742/75.

*Primary Examiner*—Natalie Trousof
*Assistant Examiner*—Jane T. Fan
*Attorney, Agent, or Firm*—David L. Rose

[57] ABSTRACT

Derivatives of the antibiotic substance milbemycin, also identified as B-41 are prepared. Milbemycin is brominated, acetylated and hydrolized in order to prepare the 13-hydroxy derivative thereof. The novel derivatives have antiparasitic activity.

4 Claims, No Drawings

DERIVATIVES OF ANTIBIOTIC SUBSTANCE MILBEMYCIN AND PROCESSES THEREFOR

BACKGROUND OF THE INVENTION

Milbemycin, or B-41 is a substance which is isolated from the fermentation broth of a milbemycin producing strain of Streptomyces. The microorganism, the fermentation conditions and the isolation procedures are more fully described in U.S. Pat. No. 3,950,360 and U.S. Pat. No. 3,984,564. The milbemycin compounds described in said patents do not have any substitution at the 13-position.

SUMMARY OF THE INVENTION

The milbemycin antibiotics are converted to 13-hydroxy milbemycins by allylic bromination which affords the 13-bromo compounds, followed by acylation to produce the 13-acyl derivatives and hydrolysis of the 13-acyl to the 13-hydroxy group. Thus, it is an object of the instant invention to describe 13-hydroxy milbemycin compounds. It is a further object to describe the processes employed to produce such compounds. A still further object of this invention is to describe the antiparasitic uses of such 13-hydroxy milbemycins. Further objects will be apparent upon reading the following description.

DESCRIPTION OF THE INVENTION

Milbemycin and the instant 13-hydroxy derivatives thereof are described by the following structural formulae:

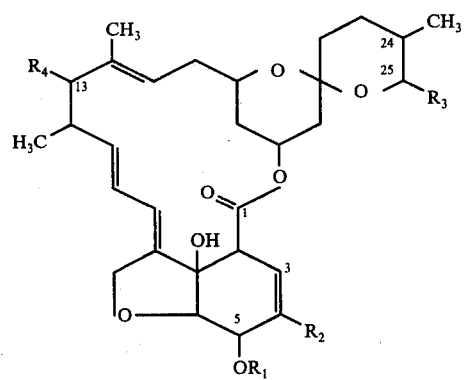

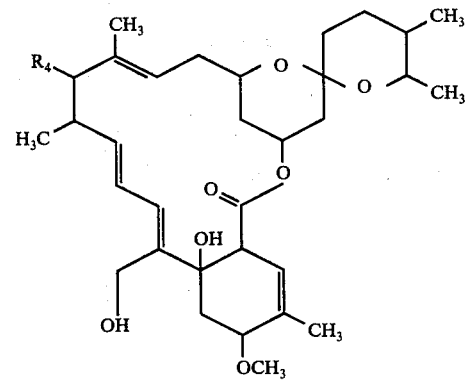

In the above formulae, when $R_4$ is hydrogen, milbemycin $A_3$, $A_4$, $B_2$, $B_3$, $C_1$, $C_2$ (for formula I) and $A_1$ (for formula II) are described. Two other milbemycin compounds, $A_2$ and $B_1$ have not yet had their structures elucidated but such compounds are believed to have structures similar to the other milbemycins. In formula I the milbemycin compounds $A_3$, $A_4$, $B_2$, $B_3$, $C_1$ and $C_2$ are defined as follows:

|       | $R_1$  | $R_2$  | $R_3$  |
|-------|--------|--------|--------|
| $A_3$ | H      | $CH_3$ | $CH_3$ |
| $A_4$ | H      | $CH_3$ | $C_2H_5$ |
| $B_2$ | $CH_3$ | $CH_3$ | $CH_3$ |
| $B_3$ | $CH_3$ | $CH_3$ | $C_2H_5$ |
| $C_1$ | H      | $-CH_2OOC-\!\!\left[\!\!\begin{array}{c}\phantom{x}\\ N\end{array}\!\!\right]$ | $CH_3$ |
| $C_2$ | H      | $-CH_2OOC-\!\!\left[\!\!\begin{array}{c}\phantom{x}\\ N\end{array}\!\!\right]$ | $C_2H_5$ |

In the foregoing formulae, the compounds of the instant invention are defined when $R_4$ is hydroxy. This position has been numbered as position 13 and such compounds are prepared from the corresponding 13-unsubstituted compounds ($R_4$=H) by the process outlined in the following reaction scheme. (Only partial structures are shown, the remainder of the molecules being as defined in formulae I and II).

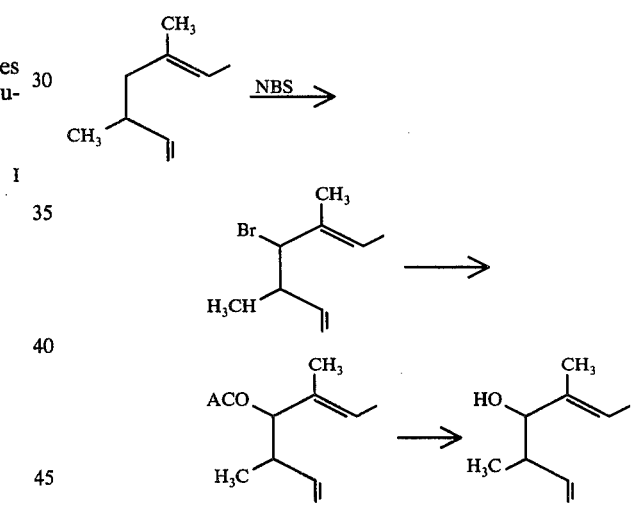

In The foregoing process NBS represents an allylic bromination reagent which preferably is N-bromosuccinimide; and $A_2$ represents an acyl group, preferably a loweralkanoyl group.

A 13-unsubstituted milbemycin is brominated using allylic bromination techniques. Preferably the process uses N-bromosuccinimide and the reaction is promoted with the use of ultraviolet light. The reaction is carried out in an inert solvent; one resistant to bromination under the conditions employed. Fully halogenated solvents, such as carbon tetrachloride are preferable. The temperature is maintained at from 0° C to about room temperature, preferably from 10° to 20° C for a period of from 10 minutes to 5 hours. Generally, the reaction is complete in from 1 to 2 hours. The product is isolated using techniques known to those skilled in this art.

The bromo compound is treated with the alkali metal acylate, preferably the alkali metal salt of a lower alkanoic acid of from 2 to 4 carbon atoms. Sodium acetate is the preferred reagent and acetic acid is the preferred solvent. The reaction is carried out at from 0° to 50° C and is generally complete in from 10 hours to 3 days. Generally, the reaction is complete in from 18 to 36 hours at about room temperature. The 13-acyloxy intermediate is isolated using known techniques.

The 13-acyloxy compound is then hydrolized to the 13-hydroxy compound. The reaction is preferably base catalyzed using an alkali metal hydroxide, preferably sodium hydroxide. The reaction is generally carried out in an aqueous medium or a mixture of water and a lower alkanol. Temperatures of from 0° C to room temperature are acceptable, however, temperatures of from 0° to 10° C are preferred. The reaction is generally complete in about 5 to 24 hours and the product is isolated using known techniques.

The following examples of the best mode contemplated of this invention are provided in order that the invention might be more fully understood. The examples are not to be construed as limitative of the instant invention.

EXAMPLE 1

13-Bromo milbemycin $B_2$

A solution of 542 mg. of milbemycin $B_2$ and 178 mg. of N-bromo succinimide in 10 ml. of carbon tetrachloride is stirred under irradiation with ultraviolet light for 1 hour at room temperature. The mixture is cooled to 0° C, the succinimide is filtered off and the solvent is removed by evaporation under reduced pressure. Chromatography of a solution of the residue in a mixture of chloroform and tetrahydrofuran (95:5) over a column of silica yields 13-bromo milbemycin $B_r$.

EXAMPLE 2

13-Acetoxy milbemycin $B_2$

A solution of 621 mg. of 13-bromo milbemycin $B_2$ and 82 mg. of anydrous sodium acetate in 10 ml. of acetic acid is stirred for 24 hours at 20°-30° C. The acetic acid is evaporated under reduced pressure and the product is separated from the sodium bromide by extraction with ether and evaporation. Chromatography of the product extracted into the ether in a mixture of chloroform and tetrahydrofuran (95:5) over a column of silica yields 13-acetoxy milbemycin $B_2$.

EXAMPLE 3

13-Hydroxy milbemycin $B_2$

A solution of 600 mg. of 13-acetoxy milbemycin $B_2$ and 44 mg. of sodium hydroxide in a mixture of 8 ml. of methanol and 2 ml. of water is stirred for 10 hours at 0°-10° C. The solvent is evaporated under reduced pressure and the residue is dissolved in chloroform. Chromatography of the chloroform solution over a column of silica yields 13-hydroxy milbemycin $B_2$.

Other milbemycin compounds such as $A_1$, $A_2$, $A_3$, $A_4$, $B_1$, $B_3$, $C_1$, $C_2$ may be similarly converted into the 13-hydroxy derivative.

The novel compounds of this invention have significant parasiticidal activity as anthelmintics, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs cats and poultry. Amoung the helminths, the group of worms described as nematodes causes widespread and often times serious infection in various species of animals. The most common genera of nematodes infecting the animals referred to above are Haemonchus, Trichostrongylus, Ostergagia, Nematodirus, Cooperia, Ascaris, Bunostomum, Oesophagostomum, Chabertia, Trichuris, Stongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still other such as Dictylocaulus are found in the lungs. Still other parasites may be located in other tissues and organs of the body such as the heart and blood vessels, subcutaneous and lymphatic tissue and the like. The parastic infections known as helminthiases lead to anemia, malnutrition, weakness, weight loss, severe damage to the walls of the intestinal tract and other tissues and organs and, if left untreated, may result in death of the infected host. The milbemycin derivatives of this invention have unexpectedly high activity against these parasites, and in addition are also active against Dirofilaria in dogs; Nematospiroides, Syphacia, Aspiculuris in rodents; arthropod ectoparasites of animals and birds such as ticks, mites, lice, fleas; blowfly, in sheep; Lucilia sp., biting insects and such migrating dipterous larvae as Hypoderma sp. in cattle; Gastrophilus in horses; and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal states of the intestinal worms Strongyloides and Trichinella. The compounds are also of value against arthropods parasitizing man, biting insects and other dipterous pests causing annoyance to man.

The compounds are also active against household pests such as the cockroach, *Blatella sp.*, clothes moth, *Tineola sp.*, carpet beetle, *Attagenus sp.* and the housefly *Musca domestica.*

The compounds are also useful against insect pests of stored grains such as *Tribolium sp., Tenebrio sp.,* and of agricultural plants such as spider mites, (*Tetranychus sp.*), aphids, (Acyrthiosiphon sp.); against migratory orthopterans such as locusts and immature stages of insects living on plant tissue. The compounds are useful as a nematocide for the control of soil nematodes and plant parasites such as *Meloidogyne spp.* which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the milbemycin compounds in a dry, solid unit dosage form, capsules, boluses or tablets containing the desired amount of active compound usually are employed. These dosage forms are prepared by intimately and uniformly mixing the active ingredient with suitable fnely divided diluents, fillers, disintegrating agents and/or binders such as starch, lactose, talc, magnesium stearate, vegetable gums and the like. Such units dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol, formal and aqueous parenteral formulations are also used. The active milbemycin derivatives are dissolved or suspended in the parenteral formulation for administration; such formulations generally contain from 0.005 to 5% by weight of the active compound.

What is claimed is:

1. 13-Hydroxy milbemycin $A_1$, $A_2$, $A_3$, $A_4$, $B_1$, $B_2$, $B_3$, $C_1$ or $C_2$.

2. 13-Bromo milbemycin $A_1$, $A_2$, $A_3$, $A_4$, $B_1$, $B_2$, $B_3$, $C_1$ or $C_2$.

3. 13-Acetoxy milbemycin $A_1$, $A_2$, $A_3$, $A_4$, $B_1$, $B_2$, $B_3$, $C_1$ or $C_2$.

4. A process for the preparation of 13-hydroxy milbemycins $A_1$, $A_2$, $A_3$, $A_4$, $B_1$, $B_2$, $B_3$, $C_1$ or $C_2$ which comprises:
   (a) brominating the 13-unsubstituted milbemycins with N-bromosuccinimide;
   (b) acetylating the 13-bromomilbemycins with an alkali metal acetate; and
   (c) hydrolizing the 13-acetoxy milbemycins with aqueous alkali metal hydroxide.

* * * * *